United States Patent

Ford et al.

Patent Number: 5,256,382
Date of Patent: Oct. 26, 1993

[54] VAPOUR-HEATED CHAMBER

[75] Inventors: Michael A. J. Ford, Bath; Christopher R. Bailey, Chobham, both of United Kingdom

[73] Assignee: Autocar Equipment Limited, London, United Kingdom

[21] Appl. No.: 741,406

[22] PCT Filed: Mar. 9, 1990

[86] PCT No.: PCT/GB90/00363
§ 371 Date: Jul. 23, 1991
§ 102(e) Date: Jul. 23, 1991

[87] PCT Pub. No.: WO90/10464
PCT Pub. Date: Sep. 20, 1990

[30] Foreign Application Priority Data

Mar. 10, 1990 [GB] United Kingdom ........ 8905495

[51] Int. Cl.⁵ .................... A61L 2/04; A61L 2/20
[52] U.S. Cl. .................... 422/307; 422/28; 422/37; 422/292; 422/298; 422/305; 219/401; 392/394; 392/400; 392/402; 392/403
[58] Field of Search .......... 422/28, 37, 292, 298, 422/305, 307; 219/401; 392/394, 403, 400, 402

[56] References Cited

U.S. PATENT DOCUMENTS

| 1,144,508 | 6/1915 | Taylor, Jr. | 392/403 |
| 2,822,459 | 2/1958 | Kamin | 392/403 |
| 4,652,408 | 3/1987 | Montgomery | 392/403 X |
| 4,697,067 | 9/1987 | Rosset et al. | 219/401 |
| 4,700,050 | 10/1987 | Hennuy et al. | 392/403 X |
| 4,710,350 | 12/1987 | Peterson | 422/37 |
| 4,909,999 | 3/1990 | Cummings | 422/30 X |

FOREIGN PATENT DOCUMENTS

| 23887 | 2/1980 | Japan | 392/403 |
| 212927 | 3/1924 | United Kingdom | 392/403 |
| 353832 | 7/1931 | United Kingdom . | |
| 476773 | 12/1937 | United Kingdom | 392/403 |
| 2160772 | 1/1986 | United Kingdom . | |

Primary Examiner—Robert J. Warden
Assistant Examiner—Stephanie Smith
Attorney, Agent, or Firm—Dann, Dorfman, Herrell & Skillman

[57] ABSTRACT

Heating apparatus comprises a chamber (10) in which articles to be heated (e.g. sterilized) are located via a door (16) and which can be filled with a blanket of dense hot organic vapor during a heating phase. The liquid which creates the vapor blanket is located in an annular reservoir (20) and is heated to above vaporization temperature by an electrical band heater (22).

10 Claims, 2 Drawing Sheets

VAPOUR-HEATED CHAMBER

TECHNICAL FIELD

This invention relates to a heating appliance which provides a vapour-heated chamber. It has particular, but not exclusive, reference to an ambient pressure steriliser capable of rapidly sterilising a small charge (e.g. up to 2 kg) of artifacts (e.g. dentist's or surgeon's tools), but can also be used for general heating applications (e.g. curing of plastics articles or vapour-phase soldering).

It is known to sterilise small artifacts in a chamber filled with the vapour of a liquid having a boiling point above 100° C. (e.g. above 150° C.), brought to boiling point in an electrically-heated reservoir forming a lower region of the chamber during a heating phase and, following a sufficient dwell time in the vapour to achieve sterilisation, to cause the vapour to condense down back into the reservoir during a condensation or cooling phase, leaving the chamber free of vapour. One example of an appliance which operates in this way is described in GB-A-2160772.

For the fastest recycling up to sterilising temperature and back to a safe handling temperature, both the heating and condensation phases need to be as short as possible. It is known to cool the chamber externally with air during the condensation phase to reduce the duration of this phase, but it is important to control the cooling process so that liquid condensate is not left on the artifacts or the trays or other platforms used to support them. It is known to locate an immersion heater directly in the liquid to reduce the duration of the heating phase, despite the risk this brings of hot spots occurring on the heater that may take the heating liquid above a recommended safe operating temperature.

It is known (see for example GB-A-353832) to use a reservoir for the heating liquid in a steriliser which has spaced-apart inner and outer walls defining therebetween a volume for the heating liquid.

SUMMARY OF THE INVENTION

According to this invention a heating appliance (and in particular a steriliser) including a vapour-heated chamber, a reservoir adapted to contain a vaporisable heating liquid and heating means for the liquid to vaporise the latter and to supply the vapour to the chamber, the reservoir having spaced-apart inner and outer walls defining therebetween a volume for the heating liquid, is characterised in that one of the inner and outer walls is used to heat the liquid during the heating phase and the other of the walls is used for cooling the liquid during the condensation phase.

Conveniently both walls are cylindrical walls (e.g. of circular cylindrical form) and are concentrically mounted with their common axis extending vertically. Suitably the inner wall is formed as an extension of a domed lower wall of the chamber, the domed lower wall being convex towards the chamber. The inner wall has a smaller surface area than the outer wall and it may be thermally more efficient to use the inner wall for transfer of heat into the reservoir and the outer wall for transfer of heat out of the reservoir. Practically however, wrapping a band heater around the outer wall is a very easy way of heating the liquid leaving the inner wall free for cooling. Air cooling is preferred, but liquid cooling (e.g. via water flows) is not excluded. Where air cooling is employed it may be desirable to improve the heat exchange coefficient of the appropriate wall of the reservoir, e.g. by the use of fins, a surface coating or a surface treatment on the reservoir wall/walls.

Where air cooling is employed, a simple fan can be located outside the chamber adjacent to the chamber walls, the air flows from the fan being used partly to cool the chamber walls and partly to cool one or both walls of the reservoir. The proportion of air used for these two purposes can remain unchanged during the condensation phase or varied (e.g. on a preset pattern) depending on the stage of cooling reached in the condensation phase.

To further reduce the time needed for the condensation phase, means can be provided to move vapour within the chamber so that enhanced vapour/cooled wall contact can be achieved. A rotatable vapour stirrer (e.g. a fan blade) can be located in the chamber and powered from a motor located outside the chamber.

A wide range of heating liquids can be used but certain halogenated organic compounds are particularly suitable heating liquids, preferably those having a boiling point above 175° C. and vapour densities at least 10 times that of air. Perfluoroperhydrofluorene ($C_{13}F_{22}$) is particularly preferred.

The size of the reservoir will be dependent on the heating liquid used but with perfluoroperhydrofluorene a volume of some 400 to 500 ml appears to be satisfactory. The surface area of the outer wall of the reservoir, for a charge of the volume stated above, could conveniently be of the order of 380 $cm^2$ and the surface area of the inner wall of the reservoir of the order of 300 $cm^2$. A band heater of some 2 KW rating wrapped around the outer wall provides a safe but fast heating with a reservoir of the size just described and with forced air cooling of the inner wall to accelerate the condensation phase, cycle times of under 20 minutes are possible for a 2 kg charge of artifacts sterilised to 190° C.

Stainless steel is a suitable material from which the reservoir walls can be formed and a wall thickness of less than 1 mm (e.g. around 0.5 mm) is preferred.

BRIEF DESCRIPTION OF DRAWINGS

One embodiment of heating apparatus according to the invention will now be described by way of example, with reference to the accompanying drawings, in which.

DESCRIPTION OF PREFERRED EMBODIMENT

Figure 1:
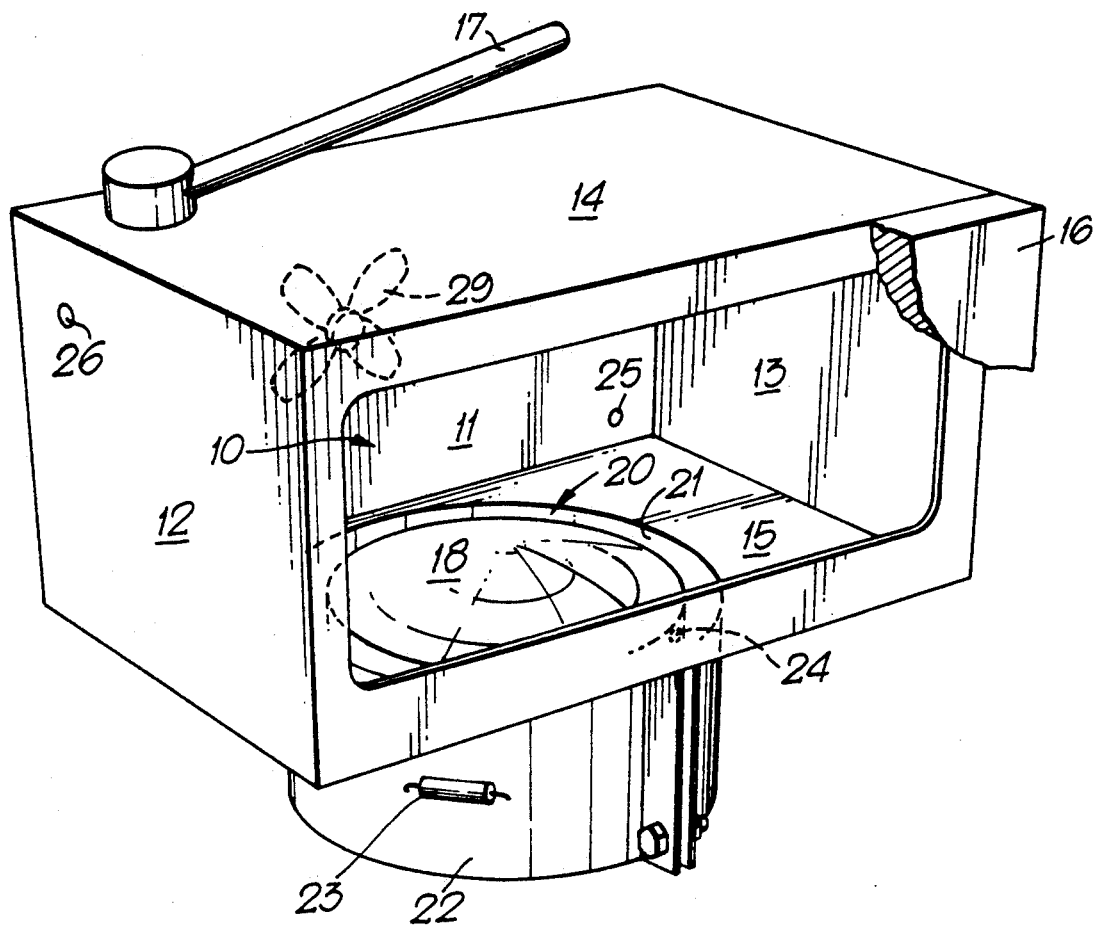
FIG. 1 is a schematic view of the apparatus with the access door shown only in part and without the decorative outer casing.
Figure 2:
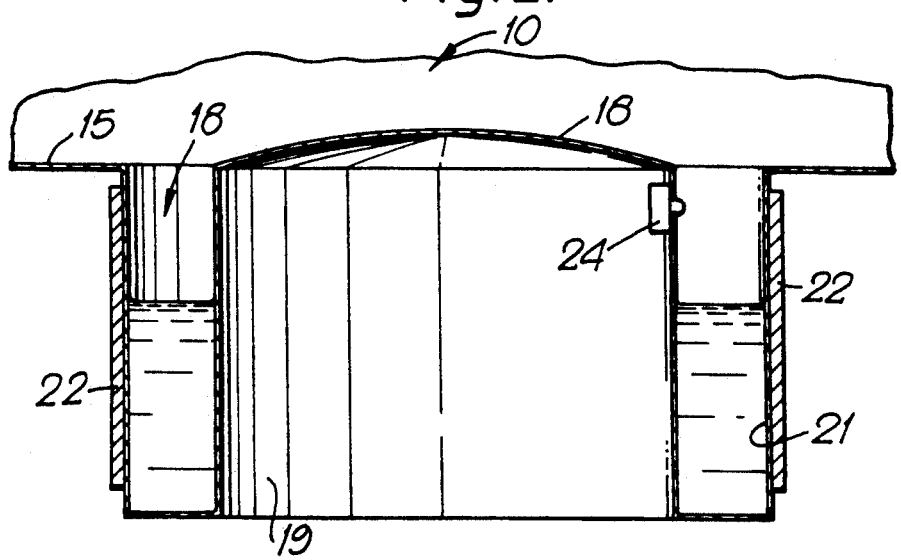
FIG. 2 is a schematic enlarged sectional view of the heating/cooling reservoir of the apparatus of FIG. 1.

The apparatus shown in FIG. 1 comprises a generally right parallelepipedic chamber 10 having a rear wall 11, side walls 12, 13, a top wall 14, a base wall 15 and a front wall which is mainly constituted by an access door 16 (shown only in part). The artifacts to be heated (e.g. dentist's tools to be sterilised) can be placed on trays (not shown) located in the chamber to slide in and out on runners mounted on the side walls 12, 13.

A breathing tube 17 communicates with the uppermost part of the chamber 10 through the top wall 14 and contains vapour condensing surfaces (e.g. glass beads)

so that as air is expelled through the tube during a heating phase, any vapour or droplets of heating liquid entrained therewith will be collected to drain back into the chamber 10. The tube 17 can be of copper to improve its performance as a condenser. A false ceiling (not shown) can be located near to the top of the chamber 10 to reduce the risk of vapour entering the breathing tube 17.

The base wall 15 is mainly constituted by a dome 18 forming the upper extremity of a cylindrical inner wall 19 of an annular reservoir 20 for heating liquid. The outer cylindrical wall 21 of the reservoir 20 supports an electrical band heater 22 with a temperature-sensitive fuse 23 in series with the heating element thereof.

Three temperature sensors 24, 25 and 26 are provided in the chamber and conveniently these are PTC (positive temperature coefficient) thermistors. Sensor 24 acts as a liquid level sensor in the reservoir 20 and is mounted in an aperture in the inner wall 19. Sensor 25 ensures the access door 16 cannot be opened after the heating phase until the temperature near the bottom of the chamber 10 has fallen to a safe level (e.g. 50°-60° C.). Sensor 26 is disposed a short distance below the false ceiling and is used to determine the end of the heating phase since it senses when it is in contact with vapour at the required high temperature. Circuitry can be employed to control the durations of the heating and condensation phases on the basis of the temperatures recorded by the sensors, but this is not described since it can be of conventional design and is not relevant to the novel aspects of this invention.

Figure 3:
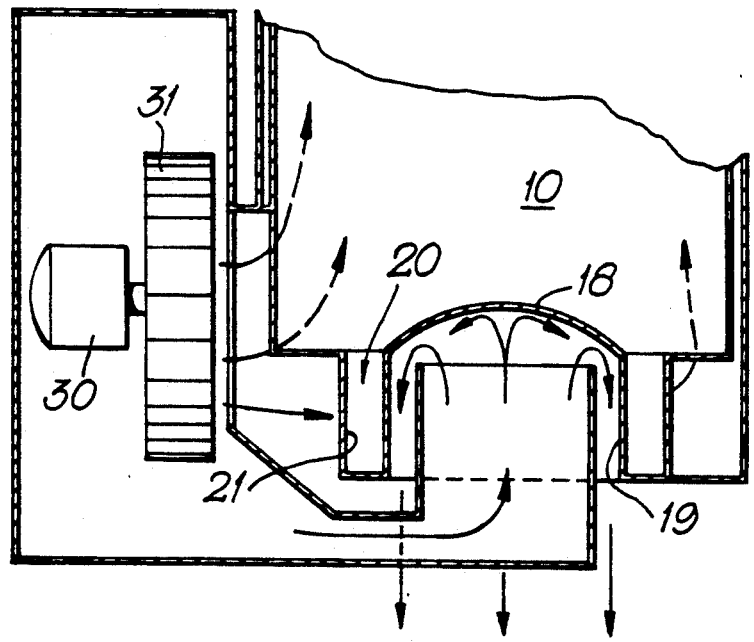
FIG. 3 is a schematic sectional view showing the cooling fan used in the apparatus of FIG. 1.

FIG. 3 shows a fan motor 30 coupled to an external centrifugal air mover 31. When the heating phase is completed, the motor 30 is energised and moves air in a first flow path that passes over the outer surfaces of the band heater and the side walls of the chamber 10 and in a second flow path that contacts the underside of the dome 18 and flows downwardly past the radially inner surface of the inner wall 19 and exits from the underside of the unit. A false floor can be provided to isolate the two flow paths and ensure that the air flows leaving the underside of the dome 18 do not mix with the air flows passing over the side walls of the chamber.

In operation of the appliance shown, following loading of the chamber with the articles to be heated and a closing of the door 16, the heater 22 is energised to rapidly raise the temperature of some 450 to 500 ml of $C_{13}F_{22}$ (e.g. a fluorocarbon liquid known under the trade name "Flutec PP10" of ISC Chemicals Limited) in the reservoir 20 to its boiling point of 190°-192° C. The vapour generated, rises as a dense blanket (the vapour density of "Flutec PP10" is almost 20 (relative to air) at its boiling point and without pressurisation) in the chamber 10 engulfing the articles supported therein. This causes the temperature of the articles to rise rapidly to the temperature of the vapour. The heating phase can be concluded a pre-set period after the blanket reaches the top sensor 26, and the fan motor 30 can then be energised. The blanket begins to subside with vapour condensing on the rear and side walls of the chamber and on the dome 18. By controlling the time during which articles in the chamber are submerged in the blanket of vapour, proper heating (e.g. sterilisation) of the articles can be ensured and by controlling the rate of heat loss from the walls 11, 12, 13, 15, 18 and 19, rapid cooling can be achieved (e.g. a full cycle in under 20 minutes) without leaving residues of liquid on the articles.

Since the condensation phase requires heat to be lost from the chamber, its duration can be reduced by forcing vapour to move within the chamber outwardly to the cooled walls. A rotatable vapour stirring device is shown at 29 in FIG. 1 and this can be powered by a motor (not shown) located outside the chamber and energised during the condensation phase. A convenient arrangement is to use a magnetic coupling between the stirring device 29 and an external driving motor (which could be the motor 30).

Almost complete return of heating liquid to the reservoir 20 can thus be achieved during the condensation phase. The heater 22 should be designed not to exceed the recommended maximum watts density for the sterilizing fluorocarbon and a 2 KW band heater having a heating area of some 350 cm² appears to achieve this well in the case of "Flutec PP10". The fact that no part of the heater comes into contact with the heating liquid is a further advantage, since even in a rare fault condition, the safe operating temperature of the liquid will not be exceeded if the fuse 23 is appropriately dimensioned.

In the particular design described, provision can be made to keep the vapour blanket at the top of the chamber 10 for a predetermined period using a micro-processor to satisfy any regulations which might be imposed (e.g. by Health Authorities, etc. regarding sterilisation time). The micro-processor can be used to cycle the band heater on and off to maintain the top of the blanket about a nominal position using closed loop control via the top sensor 26.

Although the invention has particular utility with reference to sterilising apparatus it will be appreciated that the use of a reservoir in accordance with this invention has many advantages, in other heating applications where a controlled temperature and optionally also a non-oxidising atmosphere is required. An oven similar to the chamber illustrated can be used for a wide range of heating purposes. Thus an oven for curing plastics mouldings (e.g. at temperatures upwards of 130° C.) or for effecting vapour-phase soldering (e.g. at temperatures typically 180° C. to 220° C.) can usefully be constructed based on a fluorocarbon liquid in the reservoir and other heating liquids can be used for this and other heating applications.

Among the advantages of the invention may be mentioned:

1. It is easy to design the reservoir 20 to accommodate an off-the-shelf band heater.
2. The volume of the reservoir 20 can be reduced to accommodate close to the minimum volume of liquid needed for generating the sterilising blanket.
3. The small surface area of liquid in the reservoir exposed when the door 16 is opened, reduces loss by evaporation.
4. A large surface area for heating the liquid can be obtained which is separate from a large cooling area.
5. Shorter times for the heating phase are possible.
6. Shorter times for the condensation phase are possible.
7. Very even temperature can be maintained throughout the chamber.
8. Very fast heat transfer to/from articles within the chamber can be obtained.
9. A non-oxidising atmosphere can be available during the heating phase by appropriate choice of heating liquid.

10. Plastics materials cured within a chamber heated in the manner described tend to have a better homogeneous structure.

11. Fast and efficient soldering in the hot vapour is easily achieved.

We claim:

1. In a heating appliance for cyclicly heating an article to a predetermined temperature during a heating phase of a cycle and then cooling the article during a condensation phase of the cycle, which appliance comprises a chamber having a lower part, a reservoir in the lower part of the chamber constructed to contain a vaporisable heating liquid, and heating means for heating said reservoir to vaporise any liquid therein to form vapour and to supply the vapour to the chamber, the reservoir having spaced-apart inner and outer walls defining therebetween a volume for the vaporisable heating liquid, the improvement wherein said heating means comprises means to heat one of the inner and outer walls whereby to heat the liquid, said heating means being activated during the heating phase and said apparatus comprises cooling means for cooling the other of said inner and outer walls whereby to cool the liquid, said cooling means being activated during the condensation phase.

2. A heating appliance as claimed in claim 1, wherein both said inner and outer walls are of circular cylindrical form and are coaxially mounted with their common axis extending vertically.

3. A heating appliance as claimed in claim 1, wherein said inner wall is formed as an extension of a domed floor of the chamber, the domed floor being convex towards the chamber.

4. A heating appliance as claimed in claim 1, wherein said heating means is an electrical band heater wrapped around the outer wall of the reservoir.

5. A heating appliance as claimed in claim 1, comprising fan means to move the vapour within the chamber, said fan means being activated at least during the condensation phase.

6. A heating appliance as claimed in claim 5, said fan means comprising a rotatable vapour stirrer within an upper part of the chamber.

7. A heating appliance as claimed in claim 1, said cooling means comprising a fan outside the chamber with duct means to cause a flow of air to cool said other of the walls of the reservoir.

8. A heating appliance as claimed in claim 1, said cooling means comprising a fan located outside the chamber, the air flows from the fan being used partly to cool the chamber walls above the lower part containing the reservoir, and partly to cool at least said other of said inner and outer walls of the reservoir.

9. A heating appliance as claimed in claim 1 for use as a sterilizer, said reservoir containing a volume of a halogenated organic compound comprising the vaporisable heating liquid having a boiling point above 150° C., said means to heat one of the walls comprising electric heating means for heating said volume of liquid through said one wall of the reservoir.

10. A heating appliance as claimed in claim 9, wherein the organic compound has a boiling point above 175° C. and a vapour density of at least ten times that of air.

* * * * *